United States Patent

Berg et al.

[11] Patent Number: 5,302,774
[45] Date of Patent: Apr. 12, 1994

[54] PROCESS FOR THE PRODUCTION OF BISPHENOLS

[75] Inventors: Klaus Berg; Hans-Josef Buysch, both of Krefeld; Alfred Eitel, Dormagen; Gerhard Fennhoff, Willich; Otto Immel, Krefeld; Ralf Pakull, Cologne; Bernhard Wehrle, Langenfeld; Claus Wulff, Krefeld, all of Fed. Rep. of Germany

[73] Assignee: Bayer Aktiengesellschaft, Leverkusen, Fed. Rep. of Germany

[21] Appl. No.: 103,584

[22] Filed: Aug. 9, 1993

[30] Foreign Application Priority Data

Aug. 20, 1992 [DE] Fed. Rep. of Germany ....... 4227520

[51] Int. Cl.$^5$ ............................................. C07C 39/16
[52] U.S. Cl. .................................. 568/727; 568/722; 568/723; 568/728
[58] Field of Search ............... 568/722, 724, 727, 728, 568/723

[56] References Cited

U.S. PATENT DOCUMENTS

| 2,623,908 | 12/1952 | Stosser et al. | 568/728 |
| 2,775,620 | 12/1956 | Williamson | 568/728 |
| 3,634,341 | 1/1972 | Gammill et al. | 568/722 |
| 4,391,997 | 7/1983 | Mandiratta | 568/727 |
| 4,423,252 | 12/1983 | Maki et al. | 568/728 |
| 4,847,433 | 7/1989 | Kissinger | 568/727 |
| 4,859,803 | 8/1989 | Shaw | 568/727 |
| 5,210,328 | 5/1993 | Freitag et al. | 568/721 |

FOREIGN PATENT DOCUMENTS

| 842209 | 7/1960 | United Kingdom | 568/727 |
| 849965 | 9/1960 | United Kingdom | 568/727 |
| 883391 | 11/1961 | United Kingdom | 568/727 |

Primary Examiner—Werren B. Lone
Attorney, Agent, or Firm—Connolly and Hutz

[57] ABSTRACT

The invention relates to a process for the production of bisphenols from acetone and phenols in the presence of sulfonic acid ion exchanger resins modified with alkyl-SH groups, in which 0.6 to 5% by weight $H_2O$ is added to the mixture of phenol and acetone before the reaction.

1 Claim, No Drawings

PROCESS FOR THE PRODUCTION OF BISPHENOLS

This invention relates to a process for the production of bisphenols from acetone and phenols in the presence of sulfonic acid ion exchanger resins modified with alkyl-SH groups, in which 0.6 to 5% by weight $H_2O$ is added to the mixture of phenol and acetone before the reaction.

It is known that phenols and carbonyl compounds can be condensed to form bisphenols using various catalysts, such as hydrochloric acid (U.S. Pat. Nos. 2,182,308 and 2,191,831), boron trifluoride (CA 58, 3338c), perchloric acid (CA 60, 1626h), benzenesulfonic acid (CA 59, 511h) and various cation exchanger resins (for example GB 842,209, 849,565 and 883,391). It is also known that sulfur-containing compounds can be added as co-catalysts. The use of thiodiglycolic acid and 3-mercaptopropionic acid is described, for example, in U.S. Pat. Nos. 2,468,982 and 2,623,908. The addition of alkyl mercaptans is described, for example, in U.S. Pat. No. 2,775,620 while the addition of hydrogen sulfide is described, for example, in CA 58, 1403e. On an industrial scale, known sulfur-containing catalysts can cause serious corrosion damage. The bisphenols produced in this way are contaminated with traces of catalyst and contain a high percentage of secondary products, for example condensation products isomeric to the desired bisphenol (CA = Chemical Abstracts).

By contrast, the synthesis of bisphenols, for example using ion exchanger resins modified with alkyl-SH groups in accordance with DE-A 3 619 450 or DE-A 3 727 641, enables bisphenols of high purity to be produced and isolated.

However, in the production of bisphenols from monophenols and carbonyl compounds, such as aldehydes and ketones, for example in accordance with DE-A 3 619 450 and DE-A 3 727 641, there is a considerable reduction in catalyst reactivity and selectivity after only relatively short production times. The catalyst used then has to be either regenerated or even completely renewed. This results in production stoppages and in increased work in the maintenance of the production units, i.e. in completely inadequate volume/time yields.

It has now been found that the modified ion exchanger resins retain their catalytic activity for much longer if water is added to the educt mixture of acetone and phenols in a quantity of 0.6 to 5% by weight, based on the educt mixture. In the process according to the invention, the selectivity of the reaction by which the bisphenols are formed is increased so that the purity of the bisphenols is improved by the addition of water.

This was not foreseeable, especially since it is known, for example from Angew. Chem. 75, page 662 (1963), that ion exchanger resins can only be used in dry form for the synthesis of bisphenols.

It is known, for example from EP-A 319 327, that the exchanger resins should either be dry from the outset or, in continuous operation, have to be gradually dried by dry educt mixtures if it is desired to achieve acceptable conversions and to obtain substantially isomer-free products. The same is also known of ion exchanger resins modified with alkyl-SH groups (for example EP-A 319 327, EP-A 49 411, EP-A 268 318). It is known from U.S. Pat No. 3,634,341 that exchanger resins partly neutralized with aminothiols or thiazolidines can even be sensitive to water.

Thus, according to EP-A 442 122 for example, the water formed during the reaction can be quickly and effectively removed from the reaction mixture using pervaporation membranes in order to avoid troublesome secondary reactions and effects.

Entirely satisfactory to excellent conversions and increased selectivity are obtained by the process according to the invention. This is particularly desirable because those secondary products which cannot be rearranged into p,p'-isomers, such as chromanes and indanes, are hardly formed. The isolation of relatively pure bisphenols is made easier.

The useful life of the ion exchanger resins modified with mercapto groups which can be achieved by additions of water is several times longer than that achieved where dry educts are used. Thus, distinct damage to the catalyst can generally be observed after an operating time of only 100 h where dry educt is used. This damage is reflected in a decrease in the mercapto groups in the resin. Where water-containing educts are used, substantially the same mercapto content as at the beginning is observed even after a few 1000 h. This confirms the uniform activity of the catalyst.

Accordingly, the present invention relates to a process for the production of 4,4'-dihydroxydiphenyl propanes from phenol and acetone in the presence of sulfonic acid ion exchangers modified with alkyl-SH groups, characterized in that 0.6 to 5% by weight water is added to the educt mixture of acetone and phenols before the reaction.

Suitable starting products for the process according to the invention are phenols, such as o-cresol, 2,6-dimethyl phenol, o-ethyl phenol, i-isopropyl phenol, o-tert.butyl phenol, o-phenyl phenol, but especially phenol, and ketones, such as acetone.

Suitable ion exchanger resins are sulfonated cross-linked styrene polymers and phenolic resins. Preferred ion exchanger resins are gel-form sulfonated styrene polymers which are crosslinked with 2 to 6% by weight and preferably 2 to 4% by weight divinyl benzene, based on styrene, which may even contain more than one sulfonic acid group per styrene nucleus and in which 1 to 30%, preferably 3 to 25% and more preferably 3 to 15% of the sulfonic acid groups are neutralized, for example, with aminoalkyl mercaptans, thiazolidines or aminothiophenols (for example DE-A 3 619 450, 3 727 641, EP-CA 319 327, EP-CA 268 318, DE-A 2 733 537). Aminoalkyl mercaptans and thiazolidines are preferred, cysteamine and dimethyl thiazolidine being particularly preferred. The partial neutralization of the sulfonic acids is carried out by known methods (for example DE-A 3 619 450, DE-A 3 727 641, U.S. Pat. No. 3,394,089).

Mixtures of sulfonic acid ion exchanger resins containing alkyl-SH groups (ionically or covalently bonded) may also be used.

The condensation of acetone with the phenols is carried out under conditions known per se at 50° to 100° C., preferably at 55° to 90° C. and more preferably at 55° to 85° C. with catalyst loads of 0.05 to 2.0 kg educt mixture per 1 kg resin and h, preferably 0.10 to 1.0 and, more preferably, 0.1 to 0.5 kg/l/h for molar ratios of acetone to phenol of 1:25 to 1:4. preferably 1:22 to 1:6 and, more preferably, 1:20 to 1:8.

The quantity of water added to the educt mixture is 0.6 to 5% by weight, based on the educt mixture of acetone and phenol, preferably 1.0 to 4.1% by weight and more preferably 1.2 to 2.9% by weight.

EXAMPLE 1

50 ml of a dried sulfonated styrene polymer (Lewatit SC 102) crosslinked with 2% divinyl benzene were swollen in phenol, after which 3.3 g cysteamine dissolved in phenol were added dropwise with stirring in phenolic suspension and stirring was continued for 24 h. The suspension was introduced into a heatable tube reactor into which 25 g/h of an educt mixture of phenol with 3.8% by weight acetone was pumped at 65° C., a) no water being added to the educt mixture over an operating time of 200 h and b) 1% water being added to the educt mixture over an operating time of 300 h.

The results are shown in Table 1.

TABLE 1

| | Conversion acetone | Select. for p,p'-BPA | Selectivity* |
|---|---|---|---|
| a | 98-99% | 94.2% | 0.27% |
| b | 95-96% | 94.7% | 0.12% |

*Non-rearrangeable secondary products

Accordingly, there is a significant improvement in selectivity of 0.5% and a reduction of more than 50% in the unuseable, non-isomerizable (rearrangeable) secondary products for substantially the same acetone conversion.

EXAMPLE 2

The procedure is as in Example 1 using the same catalyst, except that the temperature was increased to 70° C. and a) 1% water was added over a period of 250 h and b) 2% water was added over a period of 250 h, the conditions otherwise being the same. The result is as the same as in Example 1. When the 1% addition of water to the educt mixture is changed to 2%, there is a marginal reduction in conversion of 3 to 4%, but an increase in selectivity of 0.3% and a reduction of around 20% in the unuseable secondary products.

EXAMPLE 3

After an operating time of 1000 h, there is no reduction in the activity of the catalyst of Examples 1 and 2 where water is added.

After this operating time, the catalyst is washed with phenol and analyzed by NMR solid spectroscopy. No reduction is found in the SH group content in relation to the fresh catalyst.

However, if the same catalyst is exposed for 1000 h to a dry educt mixture, i.e. an educt mixture containing approx. 0.1% water, its activity falls by around 25% to an acetone conversion of 70 to 75% and a distinct reduction in the SH group content of around 60 to 70% is observed in the $^1$H-NMR.

We claim:

1. A process for the production of 4,4-dihydroxydiphenyl propanes from acetone and phenols in the presence of sulfonic acid ion exchangers modified with alkyl-SH groups, characterized in that 0.6 to 5% by weight water is added to the educt mixture of acetone and phenols.

* * * * *